(12) United States Patent
Scott

(10) Patent No.: US 8,791,703 B2
(45) Date of Patent: Jul. 29, 2014

(54) ELECTROSTATIC PROBES FOR MAPPING CONDUCTIVE WEB BAGGINESS

(75) Inventor: Philip A. Scott, San Jose, CA (US)

(73) Assignee: Hanergy Holding Group Ltd., Beijing (CN)

( * ) Notice: Subject to any disclaimer, the term of this patent is extended or adjusted under 35 U.S.C. 154(b) by 561 days.

(21) Appl. No.: 13/085,838

(22) Filed: Apr. 13, 2011

(65) Prior Publication Data

US 2012/0262181 A1    Oct. 18, 2012

(51) Int. Cl.
*G01N 27/60* (2006.01)

(52) U.S. Cl.
USPC .......... 324/452; 438/16; 29/890.033

(58) Field of Classification Search
CPC ........... G01N 27/60; G01N 21/9501; G01N 15/0266; Y02E 10/47; Y02E 10/50; Y02B 10/20; H01L 22/12
USPC ........ 324/452, 209, 750.23; 438/16; 29/890.033
See application file for complete search history.

(56) References Cited

U.S. PATENT DOCUMENTS

| | | | | |
|---|---|---|---|---|
| 4,004,153 A | * | 1/1977 | Obser et al. | 250/559.49 |
| 4,568,414 A | * | 2/1986 | Oldis et al. | 156/64 |
| 5,378,918 A | * | 1/1995 | Ottl | 250/559.01 |
| 5,778,724 A | * | 7/1998 | Clapp et al. | 73/159 |
| 5,816,060 A | * | 10/1998 | Brownell et al. | 62/186 |
| 5,964,988 A | * | 10/1999 | LaRose et al. | 204/164 |
| 6,009,421 A | * | 12/1999 | Xie et al. | 706/61 |
| 6,507,832 B1 | * | 1/2003 | Evans et al. | 706/61 |
| 6,707,055 B2 | * | 3/2004 | Vargas | 250/559.4 |
| 7,897,020 B2 | | 3/2011 | Mackie | |
| 2009/0145746 A1 | | 6/2009 | Hollars | |
| 2010/0133093 A1 | * | 6/2010 | MacKie et al. | 204/192.25 |
| 2010/0282276 A1 | * | 11/2010 | Kueper et al. | 134/6 |

OTHER PUBLICATIONS http://www.roisum.com/site_dev/acrobat/Baggy.pdf, dated Jan. 2001, visited Nov. 17, 2011.

* cited by examiner

*Primary Examiner* — Huy Q Phan
*Assistant Examiner* — Giovanni Astacio-Oquendo
(74) *Attorney, Agent, or Firm* — The Marbury Law Group PLLC

(57) ABSTRACT

A method for testing a conductive web includes moving a conductive web past at least one electrostatic probe, providing an alternating current or voltage which generates an alternating current to the at least one electrostatic probe, measuring a current or voltage in the at least one electrostatic probe induced by a capacitance between the conductive web and the at least one electrostatic probe, comparing the measured current or voltage to a reference value, and determining a level of bagginess of the conductive web based on the step of comparing.

22 Claims, 6 Drawing Sheets

| Current | Voltage | Capacitance | Distance | Level of Bagginess |
|---------|---------|-------------|----------|--------------------|
| $I$ | $V$ | $C$ | $X\,cm$ | Not baggy |
| $\leq I - n$ | $\leq V - n$ | $\leq C - n$ | $\leq X\,cm - y\,cm$ | Moderately baggy |
| $\geq I + n'$ | $\geq V + n'$ | $\geq C + n'$ | $\geq X\,cm + y'\,cm$ | Very baggy |

FIG. 4

ELECTROSTATIC PROBES FOR MAPPING CONDUCTIVE WEB BAGGINESS

BACKGROUND

Currently, a baggy conductive web causes significant problems in the manufacturing of photovoltaic devices on the conductive web substrate and can affect the quality of the final products. The manufacturing process of photovoltaic devices may include certain processes during which tension is applied to a conductive web as it passes between rollers. When tension is applied along the length of the conductive web during the coating process, the tension may be non-uniform in the conductive web's cross web direction, causing the web to have areas of "bagginess." Bagginess of conductive webs is also known as a lack of "tension level" in the conductive web.

SUMMARY

In the various embodiments, a method of making a photovoltaic device may include monitoring a moving conductive web, determining a level of bagginess of the conductive web and depositing a plurality of layers of the photovoltaic device on the conductive web if the level of bagginess meets a predetermined criterion. In an embodiment, the monitoring a moving conductive web may be performed using an electrostatic probe.

In the various embodiments, a method for testing a conductive web may include moving a conductive web past at least one electrostatic probe, providing an alternating current or voltage to the at least one electrostatic probe, measuring a current or voltage in the at least one electrostatic probe induced by a capacitance between the conductive web and the at least one electrostatic probe, comparing the measured current or voltage to a reference value, and determining a level of bagginess of the conductive web based on the step of comparing.

In the various embodiments, an apparatus for monitoring the bagginess of a conductive web may include at least one electrostatic probe positioned adjacent to a position where the conductive web would pass, an alternating current or voltage source electrically connected to the at least one electrostatic probe, and a processor in communication with the at least one electrostatic probe. The processor may be configured to perform steps including measuring a current or voltage in the at least one electrostatic probe induced by a capacitance between the conductive web and the at least one electrostatic probe in response to an alternating current or voltage provided to the at least one electrostatic probe, comparing the measured current or voltage to a reference value; and determining a level of bagginess of the conductive web based on the step of comparing.

In the various embodiments, an apparatus may include a first means for electrostatically monitoring a conductive web for bagginess, and a second means for determining a level of bagginess of the conductive web based on comparing a measured current or voltage in the first means induced by a capacitance between the conductive web and the first means to a stored reference value of current or voltage.

BRIEF DESCRIPTION OF THE DRAWINGS

The accompanying drawings, which are incorporated herein and constitute part of this specification, illustrate exemplary aspects of the invention, and together with the general description given above and the detailed description given below, serve to explain the features of the invention.

FIG. 4 illustrates a look-up table according to the various embodiments.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

The word "exemplary" is used herein to mean "serving as an example, instance, or illustration." Any implementation described herein as "exemplary" is not necessarily to be construed as preferred or advantageous over other implementations.

The terms "flat conductive," "conductive web," "substrate web" and "web" are used herein interchangeably and mean any material that may be used as a substrate in the photovoltaic device manufacturing.

The term "coil," is used herein to mean a conductive web that is in a roll.

In some manufacturing processes, such as photovoltaic device manufacturing, layers of material may be deposited on a moving conductive web as the web runs through rollers. The process of depositing a layer of material on a conductive web while running the conductive web through rollers may be called roll coating. This process may be used in different industries and processes, such as in the photovoltaic device (e.g., solar cell) manufacturing. Different industries use different types of roll coating processes including direct and reverse roll coating. In direct roll coating, the applicator roll rotates in the same direction as the conductive web moves. In reverse roll coating, the conductive web is fed between the rolls as a continuous coil. The applicator roll rotates in the opposite direction of the conductive web.

In manufacturing solar panels, a roll coater apparatus may run a conductive web, such as a metal web (e.g., stainless steel, aluminum, etc.) through several chambers, each chamber designed to coat the conductive web with a different layer of material (e.g., electrodes and p-type and n-type semiconductor layers for a PV device). When a conductive web is run through a roll coater machine, pressure and counter pressure are applied to the conductive web along its length to create a taut and flat surface on which the device layers may be deposited. However, when tension is applied along the length of the conductive web during the roll coating process, the conductive web may not support the applied force uniformly in the cross web direction causing it to have areas of "bagginess." Processes and apparatus for manufacturing PV devices are described in detail in Published U.S. Patent Application No. US2009/0145746 A1, filed Jan. 16, 2009, entitled "Manufacturing Apparatus and Method for Large-Scale Production of Thin-Film Solar Cells," and U.S. patent application Ser. No.

Figure 3:
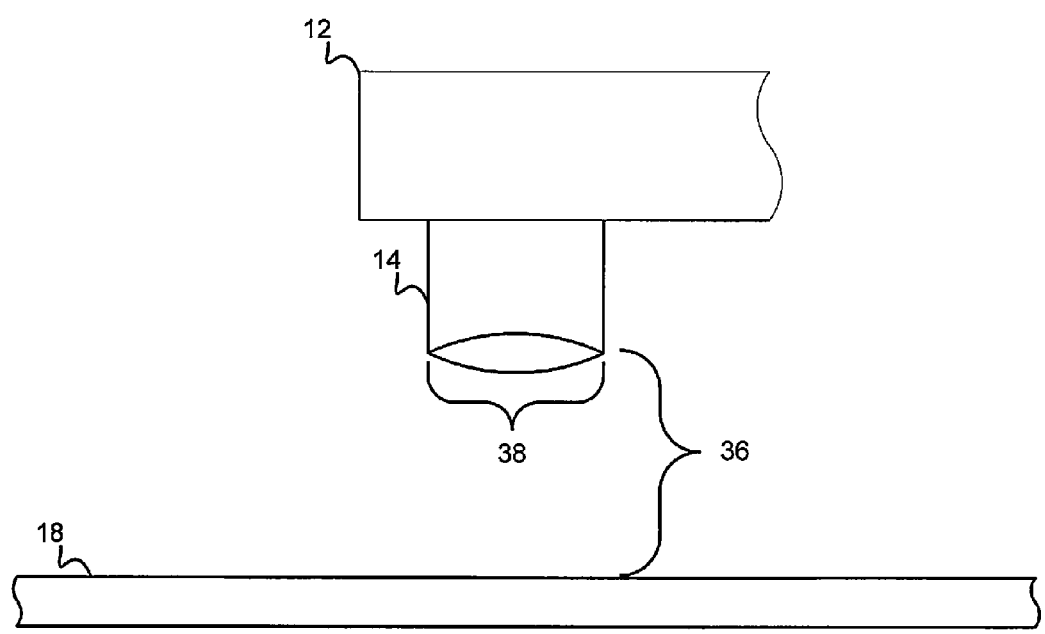
FIG. 3 illustrates a side view of one electrostatic probe of a linear array of electrostatic probes positioned adjacent to a moving conductive web, according to an embodiment.

12/385,570, filed Apr. 13, 2009, entitled "Method for Alkali Doping of Thin Film Photovoltaic Material," the entire contents of both are hereby incorporated by reference. FIG. 3 and its respective description in the specification of U.S. patent application Ser. No. 12/385,570 shows and describes an exemplary sputtering apparatus that can be used in manufacturing PV devices. It should be noted that the method described herein is not limited to solar cell manufacturing and it may be used on any web process, such as steel or other metal web processing (e.g., in the steel industry or rolling mill) which uses the bagginess metrology to improve the overall rolling process to produce webs with less bagginess.

A baggy conductive web is one that has a non-uniform geometry in its plane. Bagginess of conductive webs may also be defined in terms of the "tension level" of the conductive web. For example, a baggy conductive web is a web that lacks a uniform tension level in the cross web direction. Baggy conductive webs cause an array of problems including undesirable aesthetics, tension variations, coating variations, slitting variations, roll variations, registration errors, corona treatment errors, lateral motion, creases, and wrinkles. Because of these problems, baggy conductive webs are typically removed from the roll coater and scrapped which may in turn result in an increase in the costs for both the manufacturing company and the conductive web supplier. Furthermore, a web that is edge baggy has a potential to interfere with integrated deposition process metrology during the deposition process. Alternatively, in order to use baggy conductive webs, complex steering mechanisms with real-time feedback and numerous adjustment rollers would be required, which increases the manufacturing costs.

The various embodiment methods and apparatus provide an accurate, contact-less and continuous monitoring and mapping of the tension levels and bagginess levels of a conductive web. The methods and apparatus of the various embodiments allow for monitoring a moving conductive web, determining a level of bagginess of the conductive web and depositing a plurality of layers of material on the conductive web if the level of bagginess meets a predetermined criterion.

According to the various embodiments, different methods may be used to monitor and map tension levels of a conductive web, such as using electrostatic probes or optical devices. In an embodiment, electrostatic probes, such as electrostatic capacitance probes may be used for mapping of the entire web surface. Electrostatic probes may be used to map the position of the surface of the conductive web to screen coils for bagginess before they are subjected to the deposition or roll coating process.

In a further embodiment, mapping of the entire web surface may be performed optically. Optical devices may be used to detect variations in the dimensions and size of the web by monitoring the shape variations in the crossweb and/or downweb dimensions of the web. Optical devices include lasers, LEDs, lamps, or other light sources and photo-detectors which detect ultraviolet, infra red or visible radiation reflected from the web. In addition, the optical devices may map the web position, bagginess or lack of bagginess in a one sided or two sided array similar to the electrostatic probe arrangement described below.

The information gathered about the web tension-profile, bagginess and/or dimensions may be used to determine the usefulness of the conductive web. For example, information about the conductive web's tension-profile, bagginess and/or dimensions may be used to scrap the conductive web, or tailor the deposition process to minimize web bagginess and/or take corrective measures to eliminate the web bagginess before the layers are deposited on the web.

Figure 1:
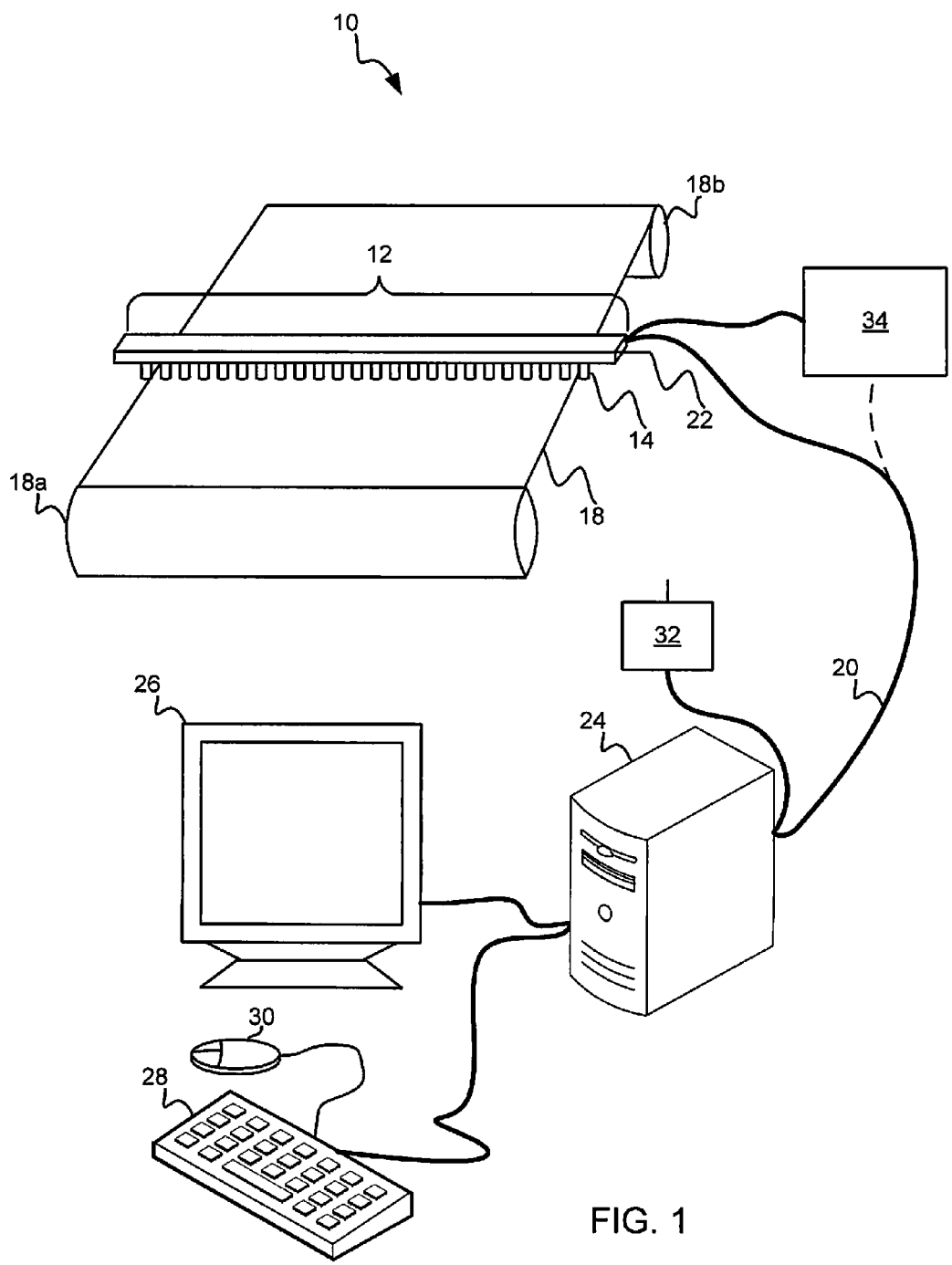
FIG. 1 schematically illustrates an electrostatic monitoring system according to an embodiment.
Figure 2:
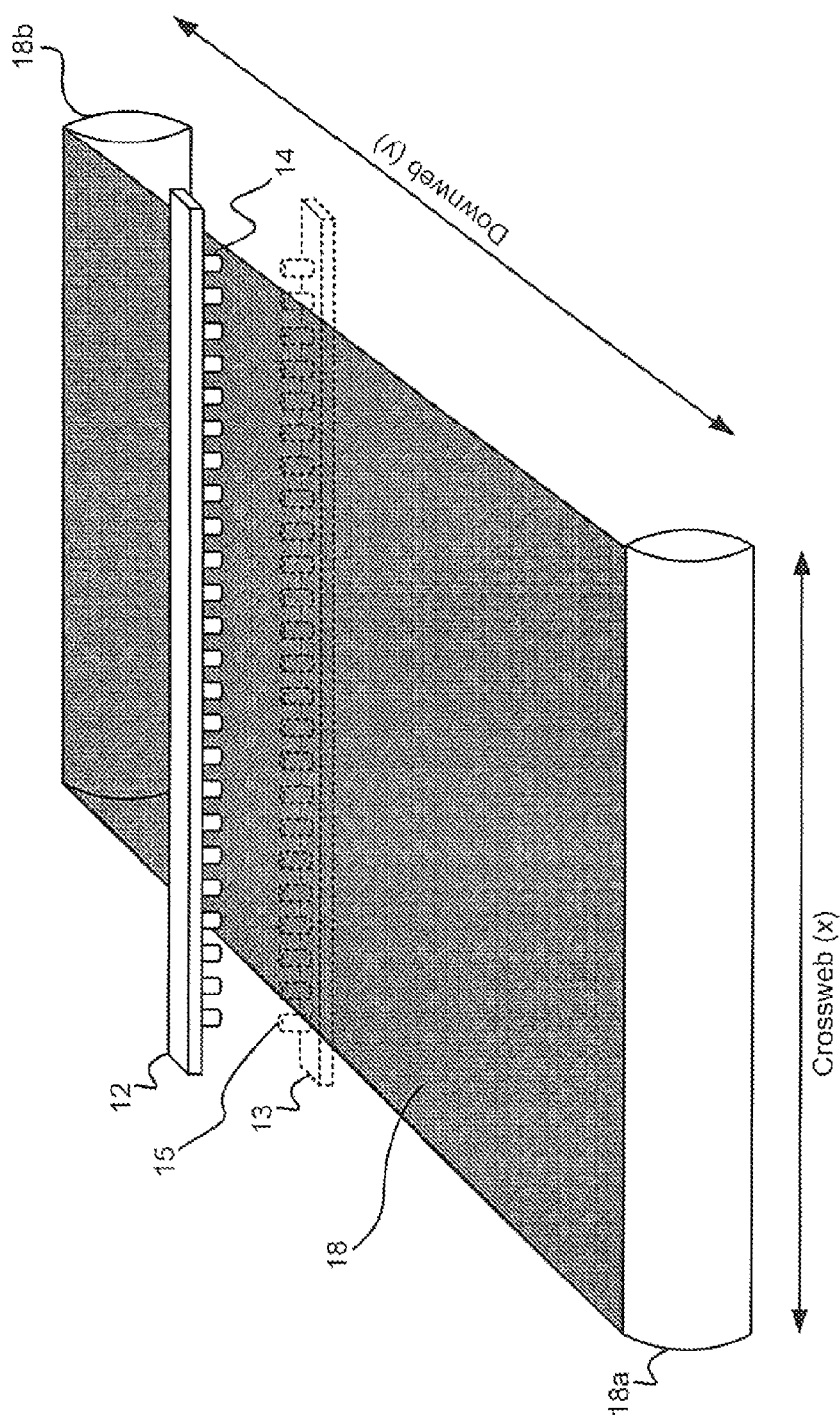
FIG. 2 illustrates a perspective view of linear arrays of electrostatic probes monitoring a moving conductive web, according to an embodiment.

In an embodiment, as illustrated in FIG. 1, an electrostatic monitoring system 10 may be used to map the tension level of a moving conductive web and detect web surface defects before the conductive web is used as a moving substrate in the photovoltaic device deposition process. To detect bagginess, at least one electrostatic probe may be used to map the position of the surface of the conductive web. The electrostatic probe 14 may be positioned in a manner to monitor the conductive web without contacting it. For example, a linear array 12 of serially arranged electrostatic probes 14 may be positioned above the moving conductive web 18. Optionally, as shown in FIG. 2, and as will be described in more detail below, an array 13 of electrostatic probes 15 may be positioned below the conductive web in addition to or instead of the linear array 12 of electrostatic probes 14 positioned above the conductive web. To allow the electrostatic probes 14 to detect surface tension levels of the web, the conductive web may be conveyed in a direction from a supply roll or input spool 18a to a wind-up roll or output spool 18b as it passes under the linear array 12 of electrostatic probes 14. If desired, spool/roll 18b may be omitted and a cutting device may cut the coated web at the end of the process into PV device sections. The process and apparatus for cutting the coated web is described in detail in the above noted U.S. patent application Ser. No. 12/385,570.

The electrostatic monitoring system 10 may be configured to allow comprehensive monitoring of the entire web surface in real-time. The real-time feedback from the electrostatic monitoring system 10 may allow for optimization of manufacturing processes, such as the roll coating process, by detecting bagginess of the conductive web 18 before the conductive web 18 undergoes the roll coating process (e.g., the PV device layer deposition). The electrostatic monitoring system 10 may monitor, in real-time, electrostatic changes that may occur due to changes in the surface of the conductive web due to bagginess.

The electrostatic monitoring system 10 may be configured to measure a current or voltage in the at least one electrostatic probe induced by a capacitance between the conductive web and the at least one electrostatic probe in response to an alternating current provided to the at least one electrostatic probe, comparing the measured current or voltage to a reference value, and determining a level of bagginess of the conductive web based on the step of comparing. The electrostatic monitoring system 10 may provide an early warning of electrostatic changes due to bagginess of the conductive web which may contribute to problems in the roll coating process.

The electrostatic monitoring system 10 may include a server 24 connected to a linear array 12 of serially arranged electrostatic probes 14. The linear array 12 of electrostatic probes may be positioned above the conductive web 18 and configured to monitor the upper surface of the conductive web 18 without coming into contact with the conductive web 18. The conductive web 18 may pass under the electrostatic probes 14 from the direction of the supply roll 18a to the wind-up roll 18b.

The linear array of electrostatic probes may be connected to a power source 34 which may be configured to supply the electrostatic probes 14 with electric power. The electric power may be supplied in different forms, such as current or voltage. The supplied electric power may be in the form of alternating current or a voltage which generates an alternating current in the probes. The power source 34 may be a grid connected power outlet, a discrete, stand-alone power generation or storage device (e.g., PV device output or battery) or an integrated device that is hardwired to its load. For example, low voltage supplies are commonly integrated with their load devices such as computers and servers 24. The power supply 34 may include a controller to turn on/off the electric power. For example, the server 24 may be used as the controller for the power supply 34. In an alternative exemplary embodiment, the server 24 may provide current or voltage to the electrostatic probes 14, thus eliminating a need for a discrete, stand-alone power supply 34 (e.g., the array 12 may be plugged into the server 24 rather than into a power outlet 34 in a wall).

The electrostatic monitoring system 10 may be configured to map the web 18 by employing the linear array of electrostatic probes to monitor and collect data about the web length in the crossweb and downweb direction. In the linear array of electrostatic probes 12, each electrostatic probe 14 may be placed next to another at a predetermined fixed distance. The separation distance between the electrostatic probes 14, the number of electrostatic probes 14 and the length covered by the linear array 13 of electrostatic probes used may vary and depend on the dimensions of the conductive web 18. In a preferred embodiment, a linear array 12 of electrostatic probes may be long enough to cover the entire length of the conductive web in crossweb direction. In such an arrangement, as the conductive web 18 passes under the linear array 12 of electrostatic probes, any variations in the surface or tension level uniformity of the conductive web may be detected by the electrostatic monitoring system 10. In an alternative embodiment, the dual array of electrostatic probes may be used to detect intended or unintended splices in the web by a thickness measurement of the web by either subtracting or adding the distances calculated using the capacitance (current or voltage measurement) measurement.

The server 24 may be configured to communicate with the linear array 12 of electrostatic probes by using a wire 20 or wirelessly. If the communication between the linear array 12 of electrostatic probes and the server 24 is through wireless connections, the linear array 12 of electrostatic probes may include an antenna 22 to transmit data from the linear array 12 of electrostatic probes to the server 24. The server 24 may be configured to receive and process data from the linear array 12 of electrostatic probes. The server 24 may include either a built-in transceiver (not shown) or be connected to an external transceiver 32. The server 24 transceiver may be configured to receive and transmit to the server 24 processor the signals transmitted from the linear array 12 of electrostatic probes.

The server 24 may be a general purpose or special purpose computer or dedicated monitoring processor or chip which will be discussed in more detail below with respect to FIG. 6. The server 24 may further be connected to a display monitor 26 for displaying data such as maps, graphs, raw data or results of calculations performed by the server 24 processor. The server 24 may also be connected to a keyboard 28 or another data input tool, and optionally to a pointing device 30 (e.g., mouse) to allow it to receive user input.

In an exemplary embodiment, the electrostatic monitoring system 10 may monitor the conductive web 18 using electrostatic probes 14 during the conductive web-washing process at a washing machine or station. Since, a conductive web 18 is usually washed before it is coated, the linear array of electrostatic probes 12 may monitor the conductive web 18 before and/or after the conductive web 18 is washed, but before the conductive web undergoes the roll coating process. In other words, the linear array 12 of electrostatic probes may be mounted in web washing station. Bagginess defects detected before the conductive web 18 is subjected to the roll coating process may be corrected (e.g., by adjusting roller tension) or simply left alone depending on their predicted effect on the roll coating process. If the bagginess defects are severe enough to cause problems in the photovoltaic cell manufacturing, and the defects are not correctable, the conductive web 18 may be scrapped.

As illustrated in FIG. 2, a first linear array 12 of electrostatic probes may be positioned above a moving conductive web 18. The first linear array 12 of electrostatic probes may be positioned in the crossweb (x) direction of the conductive web 18. Optionally, a second linear array 13 of electrostatic probes 15 may be positioned underneath and in the crossweb (x) direction of the moving conductive web 18.

FIG. 3 illustrates a side view of an electrostatic probe 14 positioned adjacent to a surface of the moving conductive web 18, according to an embodiment. When positioning a linear array 12 of electrostatic probes adjacent to the moving conductive web 18, the electrostatic probe 14 may be positioned at a predetermined distance 36 from the surface of the conductive web 18. The predetermined distance 36 between the probe 14 and the surface of the conductive web 18 may be determined as a function of the probe diameter 38. For example, the predetermined distance 36 may be about 0.5 centimeter.

Referring to FIG. 2, in an embodiment, web tension variation associated with both upper and lower surfaces of the conductive web 18 may be detected by the electrostatic monitoring system 10. In such a scenario, the first linear array 12 of electrostatic probes may be positioned adjacent to a first surface of the moving conductive web 18, and a second linear array 13 of electrostatic probes may be positioned adjacent to a second surface of the moving web 18 in a manner in which the conductive web 18 moves below the first 12 and above the second array 13 of electrostatic probes. The second array 13 of the electrostatic probes may also not come into contact with the moving conductive web 18.

As will be discussed in more detail below with respect to FIG. 5 which outlines the method of using the system 10, the electrostatic monitoring system 10 may be configured to provide an alternating current or voltage which generates an alternating current to at least one electrostatic probe 14, 15 of the first and/or second linear arrays 12, 13 of electrostatic probes, and measuring a current or voltage in the probe induced by a capacitance between the conductive web 18 and the at least one electrostatic probe 14, 15. The electrostatic monitoring system 10 may be configured to determine the level of bagginess of the conductive web 18 based on the measured current or voltage in the at least one electrostatic probe 14, 15 of the first and second linear arrays 12, 13 of electrostatic probes.

In an exemplary embodiment, electrostatic monitoring system 10 may be configured to determine the accuracy of the measurements received from each individual electrostatic probe 14, 15 by measuring the current or voltage in electrostatic probes 14, 15 from opposing linear arrays 12, 13 of electrostatic probes and compare the measured current or voltage received from a first electrostatic probe array to a second electrostatic probe array. For example, a measurement from the electrostatic probe 14 of array 12 may indicate that distance between the electrostatic probe 14 and the surface of the conductive web 18 has decreased. To confirm that this measurement points to bagginess and not an artifact created by thickness variation of the web and/or oscillation of the moving conductive web and/or mis-calibration of the electrostatic probe 18 during the roll coating process, the electrostatic monitoring system 10 may compare the measurements from the two electrostatic probes 14, 15 and determine whether the data relates to bagginess or is merely an artifact. The electrostatic monitoring system 10 may determine that a web is baggy when the distance between a first surface of the web and the electrostatic probe 15 increases or decreases proportionately to a respective decrease or increase in the distance between a second surface of the web and the electrostatic probe 14. When the distances between the electrostatic probe 14 and the first surface of the web and distance between the electrostatic probe 15 and a second surface of the web do no increase or decrease proportionately, the electrostatic monitoring system 10 may determine that such detected distance variations are due to artifacts in the web structure.

According to an embodiment, all the electrostatic probes 14, 15 on linear arrays 12, 13 of electrostatic probes may be activated simultaneously. However, electrostatic probes 14, 15 may interfere with one another if they are located in close proximity to one another and activated simultaneously. Thus, according to a further embodiment, the linear arrays 12, 13 of electrostatic probes may be configured to allow sequential activation of individual electrostatic probes 14, 15 in every array. Sequentially activating electrostatic probes 14, 15 may prevent interference that may occur between electrostatic probes 14, 15 of every array located in close proximity to one another and activated simultaneously.

According to a further embodiment, multiple electrostatic probes 14, 15 may be simultaneously activated when the activated electrostatic probes 14, 15 are separated by a distance to prevent interference. For instance, the electrostatic probes 14 located at the opposite ends of a linear array 12 of electrostatic probes may be simultaneously activated without interfering with one another.

Capacitance is the ability of a body to hold an electrical charge. Capacitance is also a measure of the amount of electric energy stored for a given electric potential. In an embodiment, the positioning of the electrostatic probes 14 with respect to the surface of the conductive web 18 may form a condition similar to that in a parallel-plate capacitor. In a parallel-plate capacitor, capacitance is directly proportional to the surface area of the conductor plates and inversely proportional to the separation distance between the plates. Accordingly, as the distance between the parallel plates (i.e., the probe 14 and the surface of the conductive web 18) increases the capacitance decreases and vice versa.

Capacitance may be calculated using different formulas:

$$C = Q/V, \quad \text{Formula I:}$$

where
C is Capacitance;
Q is the charges on the plates; and
V is voltage between the plates.

$$C = \in_r \in_0 A/d, \quad \text{Formula II:}$$

where
C is Capacitance;
A is the area overlap of the two plates;
$\in_r$ is the relative static permittivity (also known as dielectric constant) of the material between the plates (for vacuum, $\in_r = 1$);
$\in_0$ is the electric constant ($\in_0 \approx 8.854 \times 10^{-12}$ F m$^{-1}$); and
d is the separation between the plates.

The position of the web measured by the probe is given by Formula III:

$$d = (A * \hat{\in} * dV/dt)/i,$$

where
A is probe area or effective area;
$\hat{\in} = \in_r * \in_0$;
dV/dt is time rate of change of applied voltage; and
i is the current (AC) response as a result of applying voltage across gap between probe and web surface.

In an embodiment, the electrostatic monitoring system 10 may be configured to determine bagginess of a conductive web 18 under different conditions. For example, the electrostatic monitoring system 10 may determine bagginess based on measurements collected in or out of vacuum conditions.

In an embodiment, the electrostatic monitoring system 10 may be configured to employ a look-up table to determine the level of bagginess of a conductive web 18. For example, the electrostatic monitoring system 10 may be configured to measure a current of an electrostatic probe, compare the measured current value to values in a look-up table and determine the level of bagginess of the conductive web 18 based upon the measured current.

FIG. 4 illustrates an exemplary look-up table 40 which may be employed by the electrostatic monitoring system 10 to determine bagginess of a web 18. An electrostatic monitoring system 10 may provide alternating current to an electrostatic probe and the server 24 measure a current with a value of "I" in the electrostatic probe induced by a capacitance between the conductive web and the electrostatic probe. The electrostatic monitoring system 10 may be configured to compare the measured current value I to predetermined current values in column 42 of the look-up table 40. Depending on the match between the values of the measured current/and a predetermined current value in column 42, the electrostatic monitoring system 10 (e.g., server 24) may be configured to determine the level of the conductive web 18 bagginess by looking up the corresponding bagginess data in column 46. In this example, since the measured current value I matches the predetermined current value I in column 42 of the look-up table 40, the electrostatic monitoring system 10 may determine that such measured current I is consistent with a web 18 condition that is not baggy as indicated in column 46 of look-up table 40. In another similar example, if the measured current is I–n, the electrostatic monitoring system 10 may determine that the conductive web 18 is moderately baggy as indicated in column 46 of look-up table 40.

The look-up table 40 may also be used to determine other values related to a measurements obtained by the electrostatic monitoring system 10. For example, an electrostatic monitoring system 10 may measure a current I of an electrostatic probe 14 and use the look-up table 40 to determine corresponding predetermined values of voltage from column 43, capacitance from column 44 and distance from column 45. This function may be useful when the electrostatic monitoring system 10 requires different parameters, such as a distance value, to generate and display three- or two-dimensional maps or graphs of web surface. For example, the electrostatic monitoring system 10 may use a measured current value of I+n' to determine that the distance 36 between the electrostatic probe 14 and the surface of the conductive web 18 is equal to X cm+y' cm.

According to an embodiment, the electrostatic monitoring system 10 may employ an input forcing function to improve the monitoring and aid in the detection of the conductive web 18 bagginess. The intent of the input forcing function is to artificially induce flutter to the conductive web 18 to observe the relative response of baggy vs. non-baggy conductive web 18. Different methods may be used to create an input forcing function, such as by blowing a fan on the web to induce flutter.

In an embodiment, the forced air current produced by the fan may be directed towards the moving conductive web 18 in a manner to exaggerate the slack or waves in the conductive web 18. The fan may blow air on the portion of the conductive web 18 which is moving between the supply roll 18a and the wind-up roll 18b and in a direction perpendicular to the movement of the conductive web 18. The forced air current pushes together or combines low amplitude wrinkles or waves that may be present in a baggy conductive web 18 to create fewer wrinkles or waves with higher amplitudes. If the conductive web 18 is baggy, wrinkles or waves with significant amplitudes may form at the upstream portion of the conductive web 18. If the conductive web 18 is not baggy, no waves with significant amplitude may form.

In an embodiment, the electrostatic monitoring system 10 may be calibrated before monitoring the conductive web 18 for bagginess. When calibrating the electrostatic monitoring system 10, the user may measure and record the current or voltage of an electrostatic probe 14 induced by a capacitance and the distance 36 between the probe 14 and the surface of the moving conductive web 18 at different time intervals. At each measurement, the user may also determine whether the conductive web 18 is baggy.

Bagginess determination during calibration may be done using different methods. For example, an input forcing function, such as by a fan, may be used to determine bagginess of the conductive web 18 at each measurement during the calibration process. A fan may blow forced air onto a conductive web 18 to cause an exaggeration of the amplitudes of wrinkles and waves present on the web 18. The measurements and the resulting bagginess may be inputted into the server 24 of the electrostatic monitoring system 10 by the user to form the basis for determining bagginess of the conductive web 18 during the roll coating process.

The server 24 of the electrostatic monitoring system 10 may be configured to receive the inputted calibration data and store the data in a look-up table. An example of a look-up table is described above with respect to FIG. 4. In an embodiment, the look-up table 40 may be generated locally for each conductive web 18 by measuring and recording web parameters. Alternatively, pre-prepared look-up tables 40 may be provided for different types of conductive webs 18 and processes.

Figure 5:
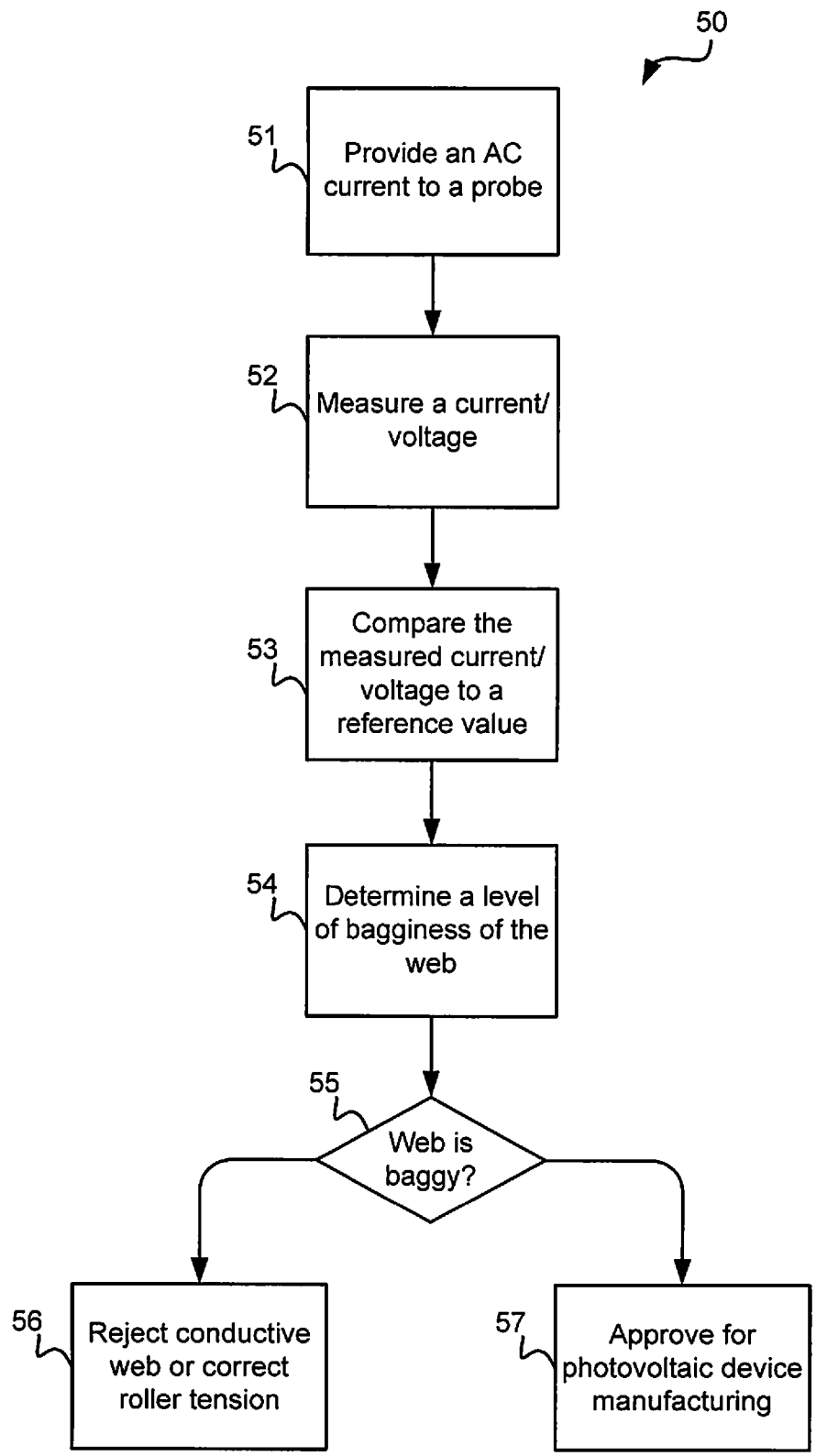
FIG. 5 illustrates a process flow diagram of an embodiment method for monitoring a conductive web.

FIG. 5 illustrates a process flow diagram 50 for monitoring a conductive web 18 for bagginess. An electrostatic monitoring system 10 may be configured to provide an alternating current or voltage which generates an alternating current to an electrostatic probe 14, step 51, and measure the current or voltage of the electrostatic probe 14 induced by a capacitance between the electrostatic probe 14 and a moving conductive web 18, step 52. The electrostatic monitoring system 10 may compare the measured current or voltage to a reference value, such as a value in a look-up table, step 53, and determine a level of bagginess of the conductive web 18 based on the comparison, step 54. The electrostatic monitoring system 10 may determine whether the conductive web 18 is baggy, determination 55. If the conductive web 18 is baggy (i.e., determination 55="Yes"), the electrostatic monitoring system 10 may reject the conductive web 18 or correct roller tension, step 56. If the conductive web 18 is not baggy (i.e., determination 55="No"), the electrostatic monitoring system 10 may approve the conductive web 18 for photovoltaic device manufacturing or another layer deposition, step 57.

Figure 6:
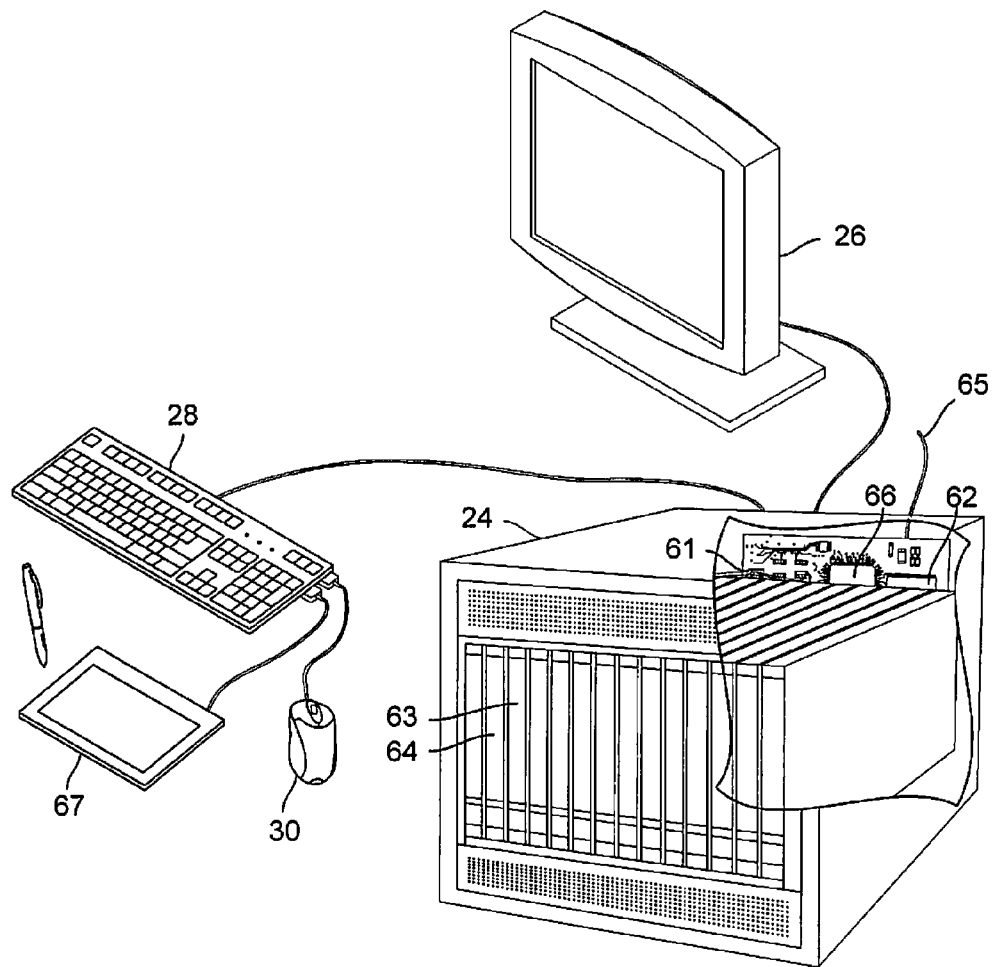
FIG. 6 illustrates a component block diagram of a server suitable for use in the various embodiments.

The various embodiments described above may be implemented on any of a variety of commercially available server devices, such as the server 24 illustrated in FIG. 6. Such a server 24 typically includes a processor 61 coupled to internal memory 62 and a large capacity nonvolatile memory, such as a disk drive or flash memory storage 63. The server 24 may also include a compact disc (CD) drive or USB input 64 coupled to the processor 61. The server 24 may also include network access ports 66 coupled to the processor 61 for establishing data connections with a network 65, such as the Internet and local networks for communicating with broadcast system equipment. The server 24 may be connected to a keyboard 28, touchpad 67 or pointing device 30 to allow users to input data into the system. The server 24 may further be connected to a monitor 26 to allow for displaying maps, graphs or other data to the users.

The processor 61 may be any programmable microprocessor, microcomputer or multiple processor chip or chips that can be configured by software instructions (applications) to perform a variety of functions, including the functions of the various embodiments described herein. Typically, software applications may be stored in the internal memory 62 before they are accessed and loaded into the processor 61. In some servers, the processor 61 may include internal memory sufficient to store the application software instructions. The internal memory 62 may be a volatile or nonvolatile memory, such as flash memory, or a mixture of both. For the purposes of this description, a general reference to memory refers to all memory accessible by the processor 61, including internal memory 62, removable memory plugged into the device (e.g., into port 64), and memory within the processor 61 itself.

The preceding description of the disclosed embodiments is provided to enable any person skilled in the art to make or use the present invention. Various modifications to these embodiments will be readily apparent to those skilled in the art, and the generic principles defined herein may be applied to other aspects without departing from the scope of the invention. Thus, the present invention is not intended to be limited to the aspects shown, the examples described and illustrations herein, but is to be accorded the widest scope consistent with the following claims and the principles and novel features disclosed herein.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

What is claimed is:

1. A method for making a photovoltaic device, comprising:
   monitoring a moving conductive web;
   determining a level of bagginess of the conductive web; and
   depositing a plurality of layers of the photovoltaic device on the conductive web if the level of bagginess meets a predetermined criteria;
   further comprising depositing the plurality of layers of the photovoltaic device on the conductive web if the level of bagginess of the conductive web is equal to or less than a predetermined level of bagginess, or rejecting the conductive web and not depositing the plurality of layers of the photovoltaic device on the conductive web if the bagginess of the conductive web is greater than the predetermined level of bagginess.

2. The method of claim 1, wherein the step of monitoring the moving conductive web is performed optically.

3. The method of claim 1, wherein the step of monitoring the moving conductive web is performed using at least one electrostatic probe.

4. The method of claim 3, wherein the at least one electrostatic probe comprises a first linear array of electrostatic probes arranged in a cross web direction adjacent to but not in contact with a first surface of the conductive web.

5. The method of claim 4, wherein the at least one electrostatic probe further comprises a second linear array of electrostatic probes arranged in a cross web direction adjacent to but not in contact with a second surface of the conductive web.

6. The method of claim 5, wherein the step of monitoring the moving conductive web comprises:
providing an alternating current or voltage which generates an alternating current to at least one electrostatic probe of the first linear array of electrostatic probes; and
measuring a current or voltage in the at least one electrostatic probe induced by a capacitance between the conductive web and the at least one electrostatic probe.

7. The method of claim 6, wherein the step of determining the level of bagginess of the conductive web comprises:
comparing the measured current or voltage to a reference value; and
determining the level of bagginess based on the step of comparing.

8. The method of claim 7, further comprising:
providing an alternating current or a voltage which generates an alternating current to at least one electrostatic probe of the second linear array of electrostatic probes;
measuring a current or voltage in the at least one electrostatic probe of the second linear array of electrostatic probes induced by a capacitance between the conductive web and the at least one electrostatic probe of the second linear array of electrostatic probe; and
checking the determined level of bagginess of the conductive web based on the measured current or voltage in the at least one electrostatic probe of the second linear array of electrostatic probes.

9. The method of claim 7, wherein:
the reference value comprises a reference value of current or voltage which corresponds to a predetermined distance between the at least one electrostatic probe and the conductive web; and
the step of determining the level of bagginess based on the step of comparing comprises determining a distance between the at least one electrostatic probe and the moving conductive web and generating the level of bagginess based on the determined distance.

10. The method of claim 9, wherein:
the reference value of current or voltage is stored in a look-up table; and
the step of generating the level of bagginess comprises generating a two dimensional map of the conductive web as a function of down web and cross web directions showing locations of bagginess.

11. The method of claim 4, wherein the step of monitoring the moving conductive web comprises:
sequentially providing an alternating current or voltage to each electrostatic probe of the linear array of electrostatic probes; and
sequentially measuring a current or voltage in each electrostatic probe induced by a capacitance between the conductive web and the at least one electrostatic probe.

12. The method of claim 1, wherein the level of bagginess of the conductive web depends on a uniformity of a tension level of the moving conductive web in a cross web direction.

13. The method of claim 1, further comprising applying an input forcing function to the conductive web.

14. The method of claim 13, wherein the input forcing function is performed by a fan.

15. A method for testing a conductive web, comprising:
moving a conductive web past at least one electrostatic probe;
providing an alternating current or voltage which generates an alternating current to the at least one electrostatic probe;
measuring a current or voltage in the at least one electrostatic probe induced by a capacitance between the conductive web and the at least one electrostatic probe;
comparing the measured current or voltage to a reference value;
determining a level of bagginess of the conductive web based on the step of comparing; and
depositing at least one layer on the conductive web if the level of bagginess of the conductive web is equal to or less than a predetermined level of bagginess; or
rejecting the conductive web if the level of bagginess of the conductive web is greater than the predetermined level of bagginess.

16. The method of claim 15, further comprising determining whether the level of bagginess of the conductive web is less than a predetermined level of bagginess.

17. The method of claim 15, wherein the at least one electrostatic probe comprises a first linear array of electrostatic probes arranged in a cross web direction adjacent to but not in contact with a first surface of the conductive web.

18. The method of claim 17, wherein the at least one electrostatic probe further comprises a second linear array of electrostatic probes arranged in a cross web direction adjacent to but not in contact with a second surface of the conductive web.

19. The method of claim 17, wherein:
the reference value comprises a reference value of current or voltage which corresponds to a predetermined distance between the at least one electrostatic probe and the conductive web; and
the step of determining the level of bagginess based on the step of comparing comprises determining a distance between the at least one electrostatic probe and the moving conductive web and generating the level of bagginess based on the determined distance.

20. The method of claim 19, wherein:
the reference value of current or voltage is stored in a look-up table; and
the step of generating the level of bagginess comprises generating a two dimensional map of the conductive web as a function of down web and cross web directions showing locations of bagginess.

21. The method of claim 17, wherein the step of monitoring the moving conductive web comprises:
sequentially providing an alternating current or voltage to each electrostatic probe of the linear array of electrostatic probes; and
sequentially measuring a current or voltage in each electrostatic probe induced by a capacitance between the conductive web and the at least one electrostatic probe.

22. The method of claim 15, wherein the level of bagginess of the conductive web depends on a uniformity of a tension level of the moving conductive web in a cross web direction.

* * * * *